United States Patent [19]

Hardman

[11] 4,046,833

[45] Sept. 6, 1977

[54] DEHYDROGENATION OF PARAFFINS

[75] Inventor: Harley F. Hardman, Lyndhurst, Ohio

[73] Assignee: The Standard Oil Company, Cleveland, Ohio

[21] Appl. No.: 643,463

[22] Filed: Dec. 22, 1975

[51] Int. Cl.$^2$ .............................................. C07C 5/18
[52] U.S. Cl. .............................. 260/683.3; 252/464; 260/680 E
[58] Field of Search ....................... 260/683.3, 680 E; 252/464

[56] References Cited

U.S. PATENT DOCUMENTS 3,856,881  12/1974  Manning ........................... 260/683.3

Primary Examiner—C. Davis
Attorney, Agent, or Firm—Herbert D. Knudsen; Evelyn R. Kosman

[57] ABSTRACT

A process for the dehydrogenation of paraffinic hydrocarbons containing from 3 to 6 carbon atoms to the corresponding monoolefin, wherein the process is carried out in the vapor phase, in the presence of oxygen and in the presence of an improved oxidative dehydrogenation catalyst containing vanadium and aluminum.

15 Claims, No Drawings

DEHYDROGENATION OF PARAFFINS

This invention relates to a process for the dehydrogenation of paraffinic hydrocarbons to the corresponding monoolefins. More particularly, this invention relates to the dehydrogenation of paraffins containing 3 to 6 carbon atoms to the corresponding monoolefin in the vapor phase in the presence of oxygen and an improved oxidative dehydrogenation catalyst.

PRIOR ART

Oxidative dehydrogenation of paraffinic hydrocarbons has been previously described in U.S. Pat. No. 3,697,614 wherein paraffins of from 2 to 12 carbon atoms are dehydrogenated to olefins with molecular oxygen in a molten alkali-metal hydroxide containing aluminum metal, and in solution, a transition metal oxyanion, preferably consisting of dichromate, molybdate, tungstate, manganate, permanganate, ferrate and metavanadate. Canadian Patent 912,051 describes a vapor phase process for the dyhydrogenation of paraffins and olefins with oxygen and halogen in the presence of a solid catalyst containing an alkali metal or an alkaline earth metal compound and a promoter which may be a transition metal of Groups 1 and 4 to 8, or a rare earth metal compound, particularly a halide or oxide of Zr, Ti, V, Cr, Mo, Mn, W, Fe, Co, Ni, Pd, Cu or Ag.

In the production of olefins by the catalytic dehydrogenation of paraffins, it is of course desirable to obtain as high a yield of olefin as possible in a single passage of the paraffin through the dehydrogenation zone. It is also desirable to conduct the reaction under such conditions and in the presence of such catalysts wherein a minimum amount of coke is formed on the catalyst. The advantage of the present process resides in the use of certain catalysts which maintains a high olefin selectivity in the presence of oxygen and wherein the oxygen is used to consume the coke. The required frequency of catalyst regeneration with the catalysts of this process is thereby greatly reduced or virtually eliminated.

THE INVENTION

The process of the present invention comprises the dehydrogenation of paraffins containing from three to six carbon atoms to the corresponding monoolefins, said dehydrogenation reaction being conducted in the vapor phase, in the presence of molecular oxygen or a molecular oxygen-containing gas, and in the presence of a catalyst containing the oxides of vanadium and aluminum and optionally one or more of the oxides of the metals of Groups IIA, IIB, VIB and VIII of the Periodic Table. The process involves passing the paraffin and oxygen at a moderate temperature over a catalyst having the following composition:

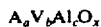

$A_a V_b Al_c O_x$ wherein
A can be one or more of the metals selected from Groups IIA, IIB, VIB and VIII of the Periodic Table, and wherein
$a$ is a number from 0 to 3,
$b$ is a number from 0.25 to 5,
$c$ is a number from 0.5 to 25, and
$x$ is a number determined by the valence requirements of the elements of A, V and Al.

Preferred are those catalysts wherein $a$ is a number from 0.1 to 1.5, $b$ is a number from 0.5 to 1.5, $c$ is a number from 1 to 16, and $x$ is a number determined by the valence requirements of the metals of A, V and Al. Especially preferred are those catalysts wherein A in the formula may be at least one element selected from the group consisting of magnesium, zinc, chromium, uranium, nickel, iron, and cobalt.

The catalyst useful in the instant process may be used alone or supported on or impregnated in a carrier material. Suitable carrier materials include alumina, silica, thoria, zirconia, titania, boron phosphate, silicon carbide, pumice, diatomaceous earth, clay, and the like. In general this support may be employed in amounts less than 95 percent by weight of the final catalyst composition.

The catalysts embodied herein may be calcined to produce desirable physical properties such as attrition resistance, optimum surface area and particle size. It is generally preferred that the calcined catalyst be further heat-treated in presence of oxygen and at a temperature above about 250° C, but below a temperature deleterious to the catalyst. The process of this invention is particularly applicable to the dehydrogenation of propane to propylene; n-butane to butene-1 and cis and trans-butene-2; isobutane to isobutylene; and isopentane to 2-methyl-2-butene, 2-methyl-1-butene and 3-methyl-1-butene. This process is also suitable for the dehydrogenation of ethylbenzene to styrene.

The reaction is carried out at elevated temperatures of from about 400° to 700° C and more preferably in the range of from 500° to 650° C.

The pressure at which the instant process is usually conducted is about one atmosphere, although pressures of from slightly below atmospheric up to about 3 atmospheres are operable.

The apparent contact time employed in the instant process may be within the range of 0.1 to 25 seconds, and for good selectivity and yields a contact time of from 1 to 15 seconds is preferred.

An essential requirement in the present process is the presence of molecular oxygen or a molecular oxygen-containing gas such as air. Suitable molar-ratios of the paraffin feed: oxygen may be in the range of from about 1:0.04 to 1:10. The preferred molar ratios of paraffin: oxygen are in the range of about 1:0.1 and 1:1. Diluent gases such as nitrogen, carbon dioxide or other inert gases may be present in minor amounts in the reaction mixture, and steam is particularly beneficial as a diluent in the reaction. Concentrations of the diluent of up to 25 moles per mole of hydrocarbon fed may be present without having any deleterious effect on the reaction.

The reactor employed in this process may be either a fixed bed or a fluidized bed reactor.

A better understanding of the invention may be derived from the following specific examples. However, it is not to be construed that the instant invention is to be limited to these examples.

SPECIFIC EXAMPLES

EXAMPLE 1

Preparation of Catalyst (A) - $V\ Al_{16.06} O_x$ 12.86 g. of $NH_4VO_3$ and 90.0 g. of Dispal M $Al_2O_3$ were combined in 500 mls. of water. The mixture was evaporated to a thick yellow paste, dried at 115° C and calcined for 4 hours at 427° C and 4 hours at 593° C.

The catalyst was placed in a 20 cc standard fixed bed reactor constructed of ½ inch O.D. stainless steel tubing.

A ⅛ inch O.D. thermocouple well, located axially, allowed for temperature profile measurement. The reactor and a pre-heat loop were immersed in a controlled temperature salt bath, and temperatures recorded were the maximum temperatures reached in the catalyst bed. The catalyst volume was 20 cc and the catalyst mesh size was 10 to 30 mesh per linear inch (U.S.A. Standard Sieve Series). The hydrocarbon feed employed in the examples was propane. A mixture of air and propane in a molar ratio of air to propane of 2.5 was passed over the catalyst at a temperature of 538° C and at a rate so that the contact time was equivalent to 3 seconds. The reactor effluent passed through an air-cooled condensation pot and a "Drierite" tube before sampling and metering. Hydrogen in the effluent stream was determined by gas chromatography, using a 3-foot molecular sieve column at ambient temperature with an argon carrier gas. Other components of the effluent were analyzed by the Fisher Partitioner, using the standard HMPA-molecular sieve column combination.

The percent conversion obtained as shown in the tables represents the total propane converted to propylene and other products (total propane converted per pass); per pass conversion to propylene represents percent of propane converted to propylene in a single pass; and selectivity to propylene is the percent of propylene obtained based on the propane converted, all percents being calculated on a molar basis.

EXAMPLE 2

The oxidative dehydrogenation procedure of Example 1 was repeated using catalyst (B) with the exception that the air:propane molar ratio was 0.2.

Preparation of Catalyst (B) - V $Cr_{0.33}Al_{5.33}O_x$ 515 g. of $Al(NO_3)_3 \cdot 9H_2O$ in 3 liters of water were gelled by adding concentrated $NH_4OH$ to a pH of 7.5. Separately, a slurry was prepared by adding a solution of 34.4 g. $Cr(NO_3)_3 \cdot 9H_2O$ to a boiling solution of 30.2 g. $NH_4VO_3$. This slurry was added to the alumina slurry and homogenized with stirring. The mixture was filtered, washed twice on the filter, dried at 110° C and calcined for 4 hours at 427° C and then for 4 hours at 649° C.

EXAMPLE 3

The oxidative dehydrogenation procedure of Example 2 was repeated using catalyst (C).

Preparation of Catalyst (C) - V $Zn_{0.5}AlO_x$ 35 g. of ZnO were dissolved in a solution of nitric acid and added to a solution of 258 g. of $Al(NO_3)_3 \cdot 9H_2O$ in water. 35 g. of $V_2O_5$ were ground in a mortar and suspended in the above solution. $NH_4OH$ was then added with stirring to a pH of 8. The slurry was filtered, washed twice on the filter, dried at 110° C and calcined for 4 hours at 427° C and 4 hours at 649° C.

EXAMPLE 4

The oxidative dehydrogenation procedure of Example 2 was repeated using catalyst (D) with the exception that the reaction temperature was 593° C and the air:propane molar ratio was 0.05.

Preparation of Catalyst (D) - V $Fe_{0.33}Al_{5.33}O_x$ 515 g. of $Al(NO_3)_3 \cdot 9H_2O$ were dissolved in 2.5 liters of water and precipitated by adding 30% $NH_4OH$ to a pH of 7.5. Separately, 26.3 g. of $NH_4VO_3$ were dissolved in 750 cc of boiling water and a solution of 30.3 g. $Fe(NO_3)_3 \cdot 9H_2O$ was added with stirring. The dark brown slurry was added to the previously prepared alumina slurry with stirring. The resulting mixture was filtered and washed twice with 500 cc of water, dried at 120° C and calcined for 4 hours at 427° C and 4.5 hours at 649° C.

EXAMPLE 5

The oxidative dehydrogenation procedure of Example 2 was repeated using catalyst (E).

Preparation of Catalyst (E) - V $Fe_{0.33}Cr_{0.72}Al_{4.30}O_x$ 412 g. $Al(NO_3)_3 \cdot 9H_2O$ and 73.8 g. of $Cr(NO_3)_3 \cdot 9H_2O$ were dissolved in 2.5 liters of water. The mixture was gelled by the addition of 30% $NH_4OH$ to a pH between 7.5–8.0. Separately, 26.3 g. of $NH_4VO_3$ were dissolved in 700 cc of boiling water and 30.3 g. of $Fe(NO_3)_3 \cdot 9H_2O$ in water were added. This slurry was added to the chromia-alumina gel with stirring, and the resulting slurry was filtered and washed twice with 500 cc of water. The solid was then dried at 120° C and calcined for 4 hours at 427° C and for 4 hours at 649° C.

EXAMPLE 6

The oxydehydrogenation procedure of Example 2 was repeated using catalyst (F).

Preparation of Catalyst (F) - V $Ni_{0.5}Cr_{0.79}Al_{4.53}Mg_{0.21}O_x$ 397 g. of $Al(NO_3) \cdot 9H_2O$ and 73.6 g. of $Cr(NO_3)_3 \cdot 9H_2O$ were dissolved in 2 liters of water and co-gelled with concentrated $NH_4OH$ added to a pH of 7.5–8.0. Separately, a slurry was prepared by adding a solution of 34 g. of $Ni(NO_3)_2 \cdot 6H_2O$, to a solution of 27.3 g. of $NH_4VO_3$. The slurry was added to the gel and homogenized with stirring, then filtered, washed twice with water and dried at 110° C. The dried catalyst was calcined for 4 hours at 427° C then impregnated with ~ 45 cc solution containing 2.9 g of $Mg(OH)_2$ in dilute nitric acid. The catalyst was again dried at 110° C and calcined for 4 hours at 649° C.

EXAMPLE 7

The oxydehydrogenation procedure of Example 2 was repeated using catalyst (G).

Preparation of Catalyst (G) - V $Fe_{0.33}Al_{5.23}Mg_{0.19}O_x$ 29.2 g. of $NH_4VO_3$ were dissolved in 1200 cc of boiling water, and a solution of 33.7 g. of $Fe(NO_3)_3 \cdot 9H_2O$ in water was added with stirring. To this slurry was added 68 g. of Dispal M alumina. The hot solution was stirred for 20 minutes (pH = 3.5) then $NH_4OH$ was added until a pH of 8 was reached. The mixture was filtered, washed twice with water while on the filter, dried at 110° C and calcined for 4 hours at 427° C. This composition was then impregnated with 2.9 g of $Mg(OH)_2$ in dilute nitric acid, dried and calcined for 4 hours at 649° C.

EXAMPLE 8

The oxydehydrogenation procedure of Example 2 was repeated using catalyst (H) with the exception that the reaction temperature was 566° C and the propane feed contained equal molar quantities of nitrogen.

Preparation of Catalyst (H) - V $Fe_{0.33}Cr_{0.72}Al_{4.15}Mg_{0.19}O_x$ 397 g. of Al(NO$_3$) .6H$_2$O and 73.9 g. CrNO$_3$.9H$_2$O were dissolved in 2.5 liters of water and gelled by the addition of NH$_4$OH to a pH of 8 with stirring. Separately 26.3 g. of NH$_4$VO$_3$ were added to 750 cc of boiling water and a solution containing 30.3 g. of Fe(-NO$_3$)$_3$.9H$_2$O was added to the NH$_4$VO$_3$ solution. After 10 minutes of stirring, the slurry was added to the chromia-alumina gel and the mixture was homogenized with stirring. The mixture was filtered, washed 3 times with water, dried at 110° C and calcined for 4 hours at 427° C. 50 g. of this composition was impregnated with a solution of 1.4544 g. of Mg(OH)$_2$ in 30 cc. of aqueous nitric acid. The impregnated catalyst was dried at 100° C and calcined for 4 hours at 427° C and 4 hours at 649° C.

The results obtained in Examples 1-8 are summarized in Table 1 below.

TABLE 1
OXIDATIVE DEHYDROGENATION OF PROPANE TO PROPYLENE IN THE PRESENCE OF VARIOUS VANADIUM-ALUMINUM CATALYSTS

| Example No. | Catalyst | % Per Pass Conversion | % Per Pass Conv. to $C_3^=$ | % Selectivity to $C_3^=$ |
|---|---|---|---|---|
| 1 | A | 22.0 | 9.1 | 41.3 |
| 2 | B | 10.8 | 8.7 | 80.5 |
| 3 | C | 7.0 | 5.3 | 76.0 |
| 4 | D | 31.9 | 24.2 | 75.8 |
| 5 | E | 13.5 | 11.5 | 85.2 |
| 6 | F | 13.9 | 11.0 | 79.1 |
| 7 | G | 12.4 | 10.4 | 83.8 |
| 8 | H | 29.0 | 23.0 | 78.3 |

EXAMPLE 9

The dehydrogenation conditions were the same as in Example 2 with the exception that the catalyst composition was that of catalyst (H) and the hydrocarbon feed was n-butane. The olefin obtained on dehydrogenation was n-butylene.

EXAMPLE 10

The catalyst composition and dehydrogenation conditions of Example 9 were repeated with the exception that the hydrocarbon feed was isobutane. The olefin obtained on dehydrogenation was isobutylene.

EXAMPLE 11

The catalyst composition and dehydrogenation conditions of Example 9 were repeated with the exception that the hydrocarbon feed was isopentane. The olefin obtained on dehydrogenation was a mixture of 2-methyl butene-1, 2-methyl butene-2, and 3-methyl butene-1.

The results obtained in Example 9 to 11 are shown in Table 2.

TABLE 2
OXIDATIVE DEHYDROGENATION OF VARIOUS PARAFFINIC FEEDS

| Example No. | % Per Pass Conversion (Total) | % Per Pass Conv. to Olefin | % Selectivity to Olefin |
|---|---|---|---|
| 9 | 13.7 | 12.4 | 90.4 |
| 10 | 21.3 | 19.7 | 92.3 |
| 11 | 18.2 | 15.4 | 84.6 |

I claim:

1. The process for the dehydrogenation of paraffinic hydrocarbons containing from 3 to 6 carbon atoms to the corresponding monoolefins comprising contacting said paraffin with molecular oxygen over a catalyst at a temperature of from about 400° to 700° C, a pressure of from about one atmosphere up to about 3 atmospheres, and wherein the molar ratio of paraffin to oxygen is in the range of from about 1:0.04 to 1:10; said catalyst having the composition:

$A_aV_bAl_cO_x$ wherein
A can be one or more of the metals selected from Groups IIA, IIB, VIB, and VIII of the Periodic Table, and
wherein
$a$ is a number from 0 to 3,
$b$ is a number from 0.25 to 5,
$c$ is a number from 0.5 to 25, and
$x$ is a number determined by the valence requirements of the metals of A, vanadium and aluminum,
and wherein said catalyst is heat-treated in the presence of oxygen.

2. The process in claim 1 wherein the contact time is in the range of from about 0.1 to 25 seconds.

3. The process in claim 2 wherein $a$ in the formula is a number from 0.1 to 1.5, $b$ is a number from 0.5 to 1.5, $c$ is a number from 1 to 16, and $x$ is a number determined by the valence requirements of the metals A, V and Al.

4. The process in claim 3 wherein A in the formula is at least one element selected from the group consisting of magnesium, zinc, chromium, uranium, nickel, iron and cobalt.

5. The process in claim 1 wherein the catalyst is supported on a carrier material.

6. The process in claim 2 wherein the paraffinic hydrocarbon is propane.

7. The process in claim 2 wherein the paraffinic hydrocarbon is isobutane.

8. The process in claim 2 wherein the paraffinic hydrocarbon is n-butane.

9. The process in claim 3 wherein steam is employed as a diluent in concentrations of up to 25 moles per mole of hydrocarbon fed.

10. The catalyst having the composition:

$A_aV_bAl_cO_x$ wherein
A is one or more of the metals selected from the group consisting of magnesium, zinc, chromium, uranium, iron, nickel and cobalt, and
wherein
$a$ is a number from 0.1 to 1.5,
$b$ is a number from 0.5 to 1.5,
$c$ is a number from 1 to 16, and
$x$ is a number determined by the valence requirements of the metals A, vanadium and aluminum;
and wherein said catalyst is heat-treated in the presence of oxygen.

11. The catalyst composition in claim 10 wherein A is at least two of the metals selected from the group consisting of magnesium, zinc, chromium, uranium, iron, nickel, and cobalt.

12. The catalyst of claim 11 wherein A is iron and chromium.

13. The catalyst of claim 11 wherein A is nickel, chromium and magnesium.

14. The catalyst of claim 11 wherein A is iron, chromium and magnesium.

15. The catalyst of claim 10 wherein A is iron.